US00PP14685P29

(12) United States Plant Patent
Sherman et al.

(10) Patent No.: US PP14,685 P2
(45) Date of Patent: Apr. 13, 2004

(54) PEACH TREE NAMED "GULFCREST"

(50) Latin Name: *Prunus persica*
Varietal Denomination: Gulfcrest

(75) Inventors: Wayne B. Sherman, Gainesville, FL (US); Gerard W. Krewer, Tifton, GA (US); Thomas G. Beckman, Byron, GA (US)

(73) Assignee: Florida Foundation Seed Producers, Inc., Greenwood, FL (US)

( * ) Notice: Subject to any disclaimer, the term of this patent is extended or adjusted under 35 U.S.C. 154(b) by 74 days.

(21) Appl. No.: 10/329,003

(22) Filed: Dec. 26, 2002

(51) Int. Cl.[7] ..... A01H 5/00
(52) U.S. Cl. ..... Plt./297

(58) Field of Search ..... Plt./197

*Primary Examiner*—Bruce R. Campell
*Assistant Examiner*—Susan B. McCormick

(57) ABSTRACT

'Gulfcrest' is a new and distinct variety of peach tree which has a moderate winter chilling requirement of approximately 525 chill units. The tree is of large size, is highly vigorous with a semi-spreading growth habit. The tree has showy pink flowers and reniform leaf glands. Trees of 'Gulfcrest' bear self-fertile flowers and regularly bear heavy annual crops which are large for the moderately early ripening season. Fruit at harvest have yellow, clingstone, non-melting flesh. Fruit are uniformly firm, attractive, substantially symmetrical shape, and have an attractive normally 90 to 95% red skin with moderately fine red stripes from tip to shoulder. The fruit ripens 4 to 5 days after 'Flordacrest' in early May at Attapulgus, Ga.

1 Drawing Sheet

BACKGROUND OF THE NEW VARIETY

The present invention relates to a new and distinct variety of peach (*Prunus persica* (L.) Batsch) tree which is named 'Gulfcrest' and, more particularly to a peach tree which produces a high percentage red skin, good eating quality, yellow, clingstone, non-melting flesh fruit which are mature for fresh market in mid-May at Attapulgus, Ga. on a tree adapted to a mid-chill winter climate. Contrast is made to 'Flordacrest' (nonpatented) peach tree, a standard variety, for reliable description. This new variety is a promising candidate for commercial success in that it retains fruit firmness at the full flavor, tree ripe stage for 5 to 7 days on the tree.

ORIGIN OF THE VARIETY

'Gulfcrest' peach tree (genotype) originated in a cultivated area of the fruit breeding program located at Attapulgus. The seed parent was Fla. 92-8c (nonpatented) and the pollen parent was 'Springbaby' nonpatented). Fla. 92-8c, a non-melting flesh peach, resulted from a cross of 'Aztec-gold' (nonpatented)×'Oro A' (nonpatented). 'Gulfcrest' peach tree was selected in 1998, and was designated and tested as AP98-10. Asexual propagation was performed at Attapulgus where the selection was made and trees were tested. Asexually propagated plants remained true to the original tree and all characteristics of the tree and the fruit were transmitted. It was propagated by budding on 'Florda-guard' (nonpatented) and 'Nemared' (nonpatented) seedling rootstocks for root-knot nematode control and determined at Attapulgus to have unique tree and fruit characteristics making it worthy for commercial fresh fruit production. There are no known effects of either rootstock on 'Gulfcrest' trees.

SUMMARY OF THE VARIETY

'Gulfcrest' peach tree is a new and distinct variety that bears a high percentage red skin over a yellow and non-melting flesh, clingstone fruit. Trees have a moderate-chilling endodormancy requirement estimated at 525 chill units. 'Gulfcrest' peach tree blooms about 7 days after 'Flordacrest' peach at Attapulgus. The present invention resulting in 'Gulfcrest' peach tree is characterized by fruit of excellent flavor and eating quality on a tree adapted to moderately mild winters. The trees are vigorous, productive and without alternate bearing. Trees attain in two years, a height of three meters and a spread of two meters at Attapulgus. Terminal growth of 0.6 to 1 meter annually is common on mature 4-year-old trees with normal pruning to a vase shape. The first fruit ripen in mid-May at Attapulgus or in about 75 to 80 days from full bloom and 4 to 5 days after the beginning of 'Flordacrest'. The fruit are uniform in size and moderately large for an early peach averaging 110 g and about 2⅜ inches diameter. Ripe fruit have 90 to 95% red skin with moderately fine darker red stripes from the tip to the shoulder. There is no red in flesh at the pit, but fruit have some red pigment in the outer flesh on the sun exposed side of the fruit. The flower petals are pink and non-showy. The anthers are light yellow.

BRIEF DESCRIPTION OF THE DRAWING

The accompanying drawing is a color photograph which shows a typical specimen of the fruit, leaf, and stem of the new variety as nearly true as it is reasonably possible to make in a color illustration of this type.

The photograph also shows a near round shape and an attractive exterior coloration of six specimens of fruit above a ruler in a stem end view, a blossom end view, side views facing and perpendicular to the suture, and fruit cut longitudinally showing the flesh with and without a pit in place.

DETAILED BOTANICAL DESCRIPTION

The tree, flowers, and fruit may vary in slight detail due to variations in soil type, cultural practices, and climatic condition. The potential for commercial production of fresh fruit by 'Gulfcrest' peach tree is high, due to its attractive red skin, yellow ground color, early ripening, good flavor balance of sugar and acid, and exceptional firmness due to its non-melting flesh. The present botanical description is that of the variety as grown on 4-year-old trees on 'Flordaguard' rootstock under the ecological conditions prevailing at Attapulgus, Ga. Variations of the usual magnitude and characteristics incident to changes in climatic growing conditions, soils, fertilization, pruning, irrigation, and pest control are to be expected. Colors (except those in common terms) are described from "The Pantone Book of Color" published by H. N. Abrams, Inc., N.Y. 1990.

Tree:

*Ploidy.*—Diploid.

*Size.*—Trees are large when trained to an open vase form.

*Vigor.*—Highly vigorous, and must be summer and winter pruned to keep tree height restricted and to keep center of vase open. Trees respond typically to irrigation and fertilization. Tree growth of 5 to 7 feet in height and 4 to 6 feet in width occurs the first 2 growing seasons in the field. Annual growth on mature trees is 2 to 3 feet in length.

*Density.*—Medium to dense in branching habit, and requires pruning to open the tree center which permits high sunlight entrance for enhancing fruit color and sugar.

*Form.*—Semi-spreading and easily pruned to the vase shape.

*Hardiness.*—Hardy with respect to typical south Georgia winters. Chill units estimated at 525 chill units.

*Bearer.*—Annual and very productive, without alternate bearing, and self fertile. Young fruit must be heavily thinned to avoid limb breakage and to obtain desired fruit size. Trees annually set several times the number of fruit for a desired crop load.

Trunk:

*Size.*—Medium trunk diameter attaining 15 cm diameter at a height of 30 cm above the ground at the end of 4 years growth at Attapulgus.

*Bark texture.*—Medium smooth, but changes to medium rough as tree ages.

*Bark color.*—Variable older bark is mostly gray, Ash (Pantone 16-3802).

*Lenticels.*—Moderate number (average of 8 per 4 square inches of surface trunk area), large (1 to 2 cm in length, perpendicular to the trunk), and flatoral (while slightly raised, lenticels are flat across the top) shape, being grey, Dove (Pantone 15-0000) and the center not opening.

Branches:

*Size.*—Vigorous growth of scaffold branches. This is not distinctive of the variety.

*Texture.*—Relatively smooth, medium amount of lenticels attaining size found on trunk and old scaffolds. Roughness increases with age.

*Color.*—New wood is light green, Leak Green (Pantone 15-0628); Three-year-old wood, Lead Gray (Pantone 17-1118).

*Blind nodes.*—Moderately low on trees grown at Attapulgus, Ga.

*Crotch angles.*—Angles selected at 45 to 80 degrees in first year of tree training. Natural angles are within the normal range of standard varieties for a semi-spreading tree.

Leaves:

*Size.*—Medium; 15 to 17 cm length, including the petiole; 33 to 37 mm width. Measurements on mature leaves from terminal shoots of summer growth.

*Thickness.*—Regular and average for peach varieties. Not distinctive of the variety.

*Form.*—Lanceolate with an acuminate apex and cuneate base. Margins are serrulate, slightly undulate.

*Surface.*—Upper, glabrous; Lower, medium large veins that are pinnately netted.

*Color.*—Lower — Green, Willow (Pantone 16-0632); Upper — Green, Lizard (Pantone 18-0629). Veins on lower surface of old leaves and into the petiole showing moderate anthocyanin development in late summer to autumn as is typical of an 80 day peach variety.

*Glands.*—Two to four globose glands mostly on the base of the leaf blade. Leaf glands are moderate size for many peach varieties and are not distinctive for the variety. Leaf glands on young leaves are light green, Pale Star (Pantone 12-0626), darkening to brown on older leaves in mid-summer.

*Petiole.*—Medium long, 12 to 14 mm length; 1.5 mm diameter. Light green, Willow Green (Pantone 15-0525) on young leaves upon becoming full size, darkening on older leaves.

*Stipules.*—Medium in length (5 to 8 mm) and early deciduous, abscising just before leaf obtains full size on summer growth. There are 2 stipules per node.

*Arrangement.*—Alternate.

Flower buds:

*Hardiness.*—Hardy in north central Florida winters. No damage observed at 14 F.

*Abundance.*—Moderately high, most buds set fruit in absence of spring frosts.

*Size.*—Medium, average 3.5 mm length in early winter.

*Form.*—Plump, conic and free.

*Surface.*—Pubescent scales.

*Color.*—Brown, Cocoa Brown, (Pantone 18-1222 ) in late autumn.

Flowers:

*Blossom period.*—Beginning with 'Sunfre' nectarine — average February 19 to 23th at Attapulgus and occurring over a 7 to 10 day period, dependant on ambient temperatures.

*Aroma.*—Fragrance is slight to none as is typical of most peaches grown for commercial fruit.

*Type.*—Non-showy, location and seasonally variable, 28 mm average diameter, but within the midrange size of non-showy flower. Petal length, 12 mm average; width, 8 mm average. Petals are obovate and edges vary from smooth to slightly undulate.

*Flower parts.*—Pistil shape and color are within the range of standard commercial varieties. There are 5 petals and 5 sepals. Sepals are pubescent and petals glabrous. Pistils are usually 1 per flower and pubescent. Pistil length (from tip of stigma to base of the ovary) is 13 to 15 mm and color is green, Pale Star (Pantone 12-0626). Flower pedicel is 4 to 6 mm length, not distinguishing for the variety.

*Stamens.*—Number varies from 26 to 33. Length is 8 to 10 mm.

*Color.*—Pink, Rose Shadow (Pantone 13-1906) when first open. Upper and lower surface are similar color.

*Anthers.*—Yellow, Apricot Nectar (Pantone 14-1133) at flower opening, darkest when flowers begin opening and fading before pollen is shed, regular size. Size is not uniquely different than that of most self fertile peach varieties.

*Pollen.*—Abundant and bright yellow, Snapdragon (Pantone 13-0840).

*Fertility.*—Self fertile and no cross pollination is required.

*Calyx cup.*—Medium size as compared to commercial varieties. Depth is 4 mm; width at top is 5 mm.

Fruit:

*Maturity when described.*—Tree-ripe, May 13, 2002 at Attapulgus.

*Date of first picking.*—May 13, 2002 at Attapulgus (normal).

*Date of last picking.*—May 20, 2002 at Attapulgus.

*Size.*—Uniform, medium large (large size for early maturity at 110 to 120 grams), varies with number of fruit per tree, soil type, climatic conditions and cultural practices.

*Average diameter axially.*—2⅜ inches (60 mm).

*Average length.*—2½ inches (63 mm).

*Pubescence.*—Medium, about the same as for 'Flordacrest'.

*Pedicel.*—Medium size. Length is 9 mm; Width is 3.5 mm. Color is pale green, Leek Green (Pantone 15-0628).

*Longitudinal section form.*—Nearly round with slight point.

*Transverse section through diameter.*—Nearly round.

*Suture.*—Shallow and inconspicuous, but usually cleft at the stem end.

*Ventral surface.*—Rounded.

*Base.*—Slightly retuse.

*Apex.*—Round to slight point.

*Cavity at pit.*—No cavity at pit in clingstone fruit.

*Crater at pedicel attachment.*—Flaring circular with stem depressing on base of fruit. Depth is 10 mm; Breadth is 15 to 20 mm at top and 4 to5 mm at pedicel attachment.

Skin:

*Thickness.*—Medium in comparison to commercial peach varieties.

*Texture.*—Medium in comparison to commercial peach varieties.

*Tenacity.*—Tenacious to the flesh even at soft ripe.

*Color.*—Red, Paprika (Pantone 17-1553) over 90 to 100% of skin with darker fine red stripes from tip to the shoulder of the fruit. Ground color is deep yellow, Saffron (Pantone 14-1064). Fruit exposed to sunlight have a higher intensity of red skin.

*Tendency to crack.*—None observed.

*Taste.*—No astringency observed.

*Pubescence.*—Medium. Shorter and softer to the touch in comparison to 'Flordacrest'.

Flesh:

*Ripens.*—Evenly within each fruit and throughout the tree.

*Texture.*—Firm, fine, juicy, non-melting with few fibers noticeable when fully ripe.

*Fibers.*—Very fine, small, tender, and abundant throughout the flesh.

*Aroma.*—Moderate and in the middle range of commercial peach varieties.

*Eating quality.*—Good, sweet and slightly acid. Fruit has averaged near 12 brix when described at harvest date. Titratable acidity was 0.82 as % malic acid and penetrometer firmness with a standard 8 mm tip was 1.4 kg at harvest;

*Juice.*—Abundant.

*Color.*—Flesh is yellow, Sunset Gold (Pantone 13-0940) with some redness, Crimson (Pantone 19-1762) throughout the flesh, especially on stressed trees under dry, hot conditions. There is no red at the pit.

*Browning by oxidation.*—Slight on tree ripe fruit beginning to soften.

*Amygdaline.*—Undetected by taste.

Stone:

*Type.*—Clingstone, but beginning to separate from the flesh in overripe fruit.

*Size.*—Medium small; average length is 30 mm, average width at the equator perpendicular (dorsal to ventral side) to the suture is 23 mm, and average width at the equator across (facing) the suture is 15 mm. Average pit wall thickness at the equator and perpendicular to the suture is 5 to 6 mm.

*Color.*—Dull yellow, Banana (Pantone 13-0947) when freshly exposed.

*Form.*—Elliptic shape with an acuminate tip and acute base. Sides are near equal.

*Surface.*—Irregularly furrowed toward the ventral edge, pitted from the center toward the base and apex. Ridges are jagged on suture toward the base of pit.

*Tendency to split.*—None observed.

*Kernel.*—Oval shape, bitter (amygdalin is abundant), and viable for germination with embryo culture. Width averages10 mm and length 15 mm. Seed coat is brown, Caramel (Pantone 16-1439) when first removed from stone of freshly harvested mature fruit.

Use: Fresh; dessert.

Resistance to disease: High resistance to bacterial spot incited by *Xanthomonas campestris* pv. *pruni* (Smith) Dye. No unusual resistance or susceptibility to insects and diseases noted.

Keeping quality: Excellent after 2 weeks at 2 C and with minimal bruises or scarring on skin.

Shipping quality: Degree of firmness at harvest and firmness retained in refrigeration at 2 C with no internal breakdown of flesh or appreciable loss of eating quality indicates fruit should be highly acceptable for shipping.

We claim:

1. A new and distinct peach tree variety as illustrated and described, characterized by a moderate chilling requirement, and bearing early-ripening fruit with firm, yellow and non-melting flesh of high eating quality and an attractive, high percentage red skin color with fruit ripening in mid-May or 4 to 5 days after 'Flordacrest' at Attapulgus, Ga.

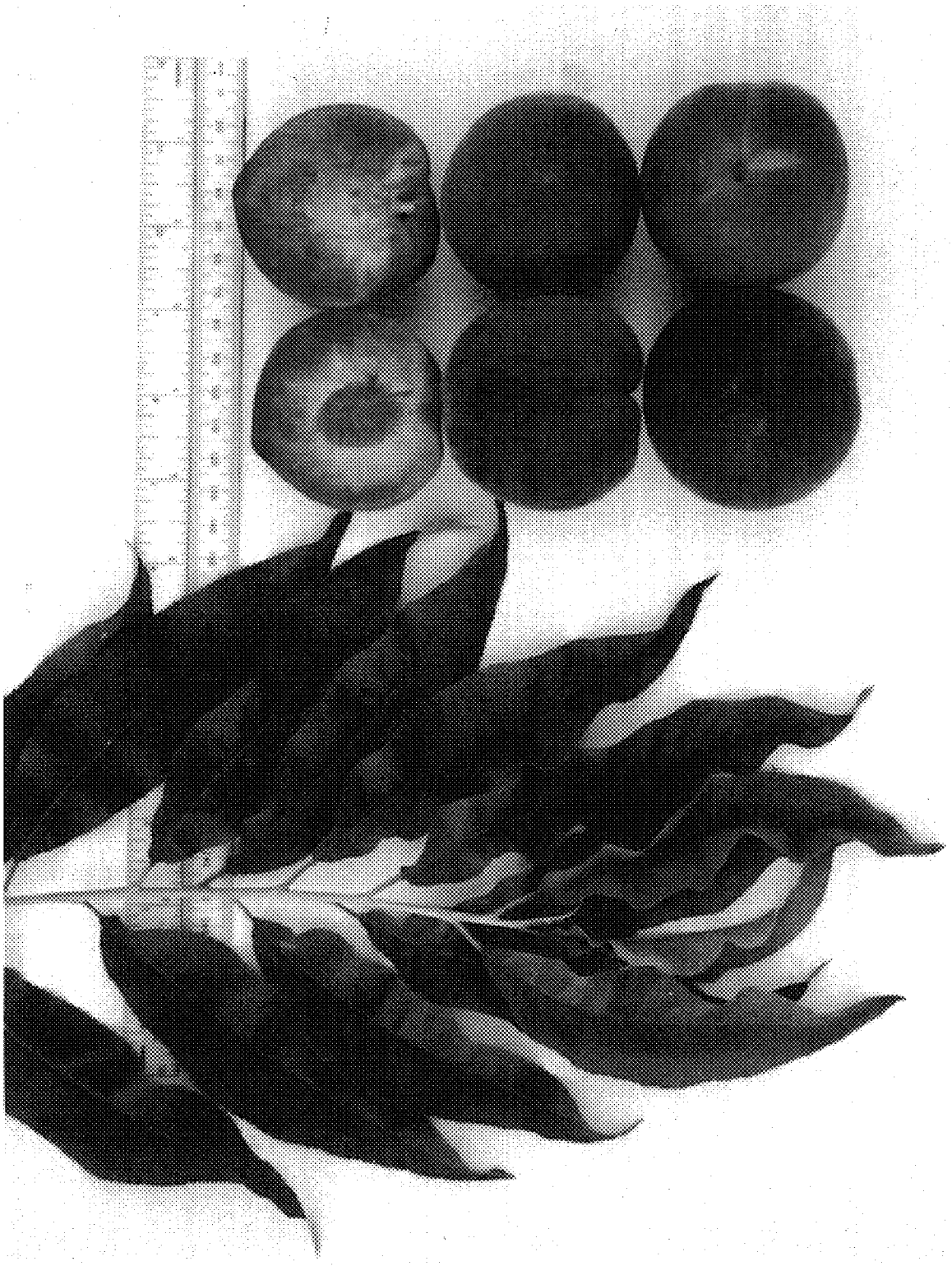

* * * * *